(12) United States Patent
Bornzin et al.

(10) Patent No.: US 12,599,771 B2
(45) Date of Patent: Apr. 14, 2026

(54) METHODS AND DEVICES FOR IMPROVED EVOKED RESPONSE DETECTION

(71) Applicant: Pacesetter, Inc., Sylmar, CA (US)

(72) Inventors: Gene A. Bornzin, Santa Monica, CA (US); Alexander R. Bornzin, Ventura, CA (US)

(73) Assignee: Pacesetter, Inc., Sylmar, CA (US)

( * ) Notice: Subject to any disclaimer, the term of this patent is extended or adjusted under 35 U.S.C. 154(b) by 370 days.

(21) Appl. No.: 18/478,799

(22) Filed: Sep. 29, 2023

(65) Prior Publication Data

US 2024/0157154 A1 May 16, 2024

Related U.S. Application Data

(60) Provisional application No. 63/425,422, filed on Nov. 15, 2022.

(51) Int. Cl.
*A61N 1/365* (2006.01)
(52) U.S. Cl.
CPC .................................. *A61N 1/36514* (2013.01)
(58) Field of Classification Search
CPC ... A61N 1/36514; A61N 1/371; A61N 1/3756
See application file for complete search history.

(56) References Cited

U.S. PATENT DOCUMENTS

| | | |
|---|---|---|
| 4,991,583 A | 2/1991 | Silvian |
| 5,178,140 A | 1/1993 | Ibrahim |
| 5,486,201 A | 1/1996 | Canfield |
| 5,694,949 A | 12/1997 | Reggiardo |
| 5,716,381 A | 2/1998 | Reggiardo |
| 5,893,049 A | 4/1999 | Reggiardo |
| 8,725,256 B2 | 5/2014 | Moulder et al. |
| 9,026,208 B2 | 5/2015 | Morley et al. |
| 9,233,250 B2 | 1/2016 | Shelchuk et al. |
| 9,345,882 B2 | 5/2016 | Moulder et al. |
| 9,616,240 B2 | 4/2017 | Labbe et al. |

(Continued)

OTHER PUBLICATIONS

Boriani, Giuseppe, et al., "Atrial Evoked Response Integral for Automatic Capture Verification in Atrial Pacing," PACE, vol. 26, Part II, Jan. 2003, 7 pages.

(Continued)

*Primary Examiner* — Rex R Holmes
(74) *Attorney, Agent, or Firm* — Pearl Cohen Zedek Latzer Baratz LLP

(57) ABSTRACT

Described herein are implantable medical devices (IMDs), and methods for use therewith. In certain embodiments, a controller of an IMD controls when a pacing capacitor of the IMD is charged using a first voltage, when the pacing capacitor is being charged using a second voltage, and when the pacing capacitor is discharged to deliver a pacing pulse between anode and cathode electrodes of, or electrically coupled to, the IMD. By selectively charging the pacing capacitor for a portion of a charge duration using the second voltage, that is greater in magnitude than the first voltage that is used for delivering the pacing pulse, a magnitude of a polarization artifact superimposed on an evoked response within a cardiac electrical signal, sensed using a sensing circuit of the IMD, is reduced compared to if the pacing capacitor were instead charged using the first voltage for the entire charge duration.

25 Claims, 6 Drawing Sheets

(56)                    References Cited

U.S. PATENT DOCUMENTS

| | | |
|---|---|---|
| 10,456,582 B2 | 10/2019 | Xing |
| 2021/0308466 A1 | 10/2021 | Bornzin |
| 2021/0308472 A1 | 10/2021 | Bornzin et al. |

OTHER PUBLICATIONS

Sperzel, Johannes, et al., "Evaluation of the Atrial Evoked Response for Capture Detection with High-Polarization Leads," PACE, vol. 28, Supplement 1, Jan. 2005, 7 pages.
Binner, Ludwig, et al., "Autocapture Enhancements: Unipolar and Bipolar Lead Compatibility and Bipolar Pacing Capabiilty on Bipolar Leads," PACE, vol. 26, Part II, Jan. 2003, 6 pages.
Stokes, Ken, et al., "The Electrode-Biointerface Stimulation," Modern Cardiac Pacing, Chapter 3, Aug. 1985, 45 pages.
Bornzin, Gene, et al., "The Electrode-Biointerface: Sensing," Modern Cardiac Pacing, Chapter 3, Aug. 1985, 45 pages.

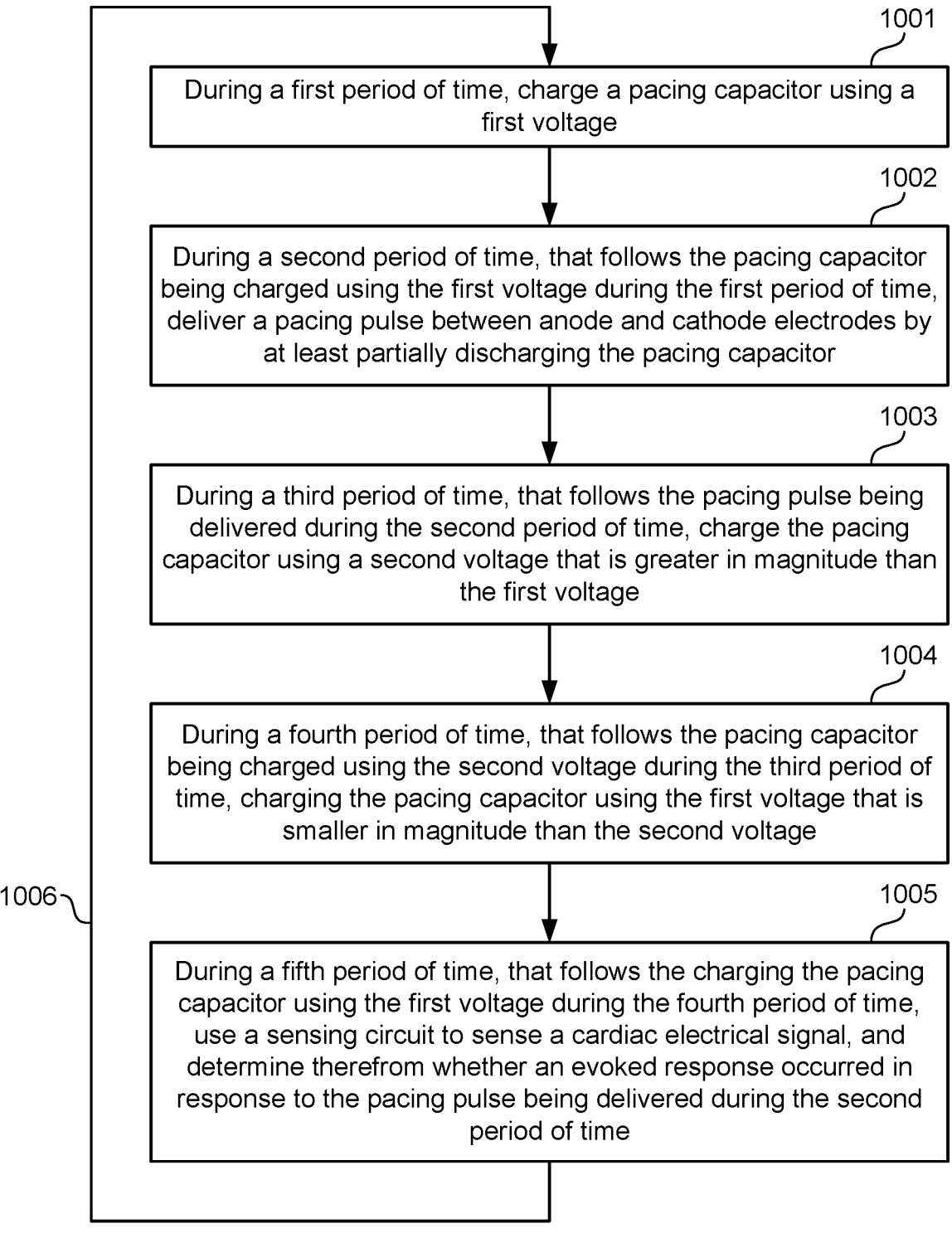

1001

During a first period of time, charge a pacing capacitor using a first voltage

1002

During a second period of time, that follows the pacing capacitor being charged using the first voltage during the first period of time, deliver a pacing pulse between anode and cathode electrodes by at least partially discharging the pacing capacitor

1003

During a third period of time, that follows the pacing pulse being delivered during the second period of time, charge the pacing capacitor using a second voltage that is greater in magnitude than the first voltage

1004

During a fourth period of time, that follows the pacing capacitor being charged using the second voltage during the third period of time, charging the pacing capacitor using the first voltage that is smaller in magnitude than the second voltage

1006

1005

During a fifth period of time, that follows the charging the pacing capacitor using the first voltage during the fourth period of time, use a sensing circuit to sense a cardiac electrical signal, and determine therefrom whether an evoked response occurred in response to the pacing pulse being delivered during the second period of time

*FIG. 10*

METHODS AND DEVICES FOR IMPROVED EVOKED RESPONSE DETECTION

PRIORITY CLAIM

This application claims priority to U.S. Provisional Patent Application No. 63/425,422, filed Nov. 15, 2022, which is incorporated herein by reference in its entirety.

FIELD

Embodiments of the present technology described herein generally relate to implantable medical devices (IMDs), and more particularly, IMDs that have pacing capabilities, such as pacemakers, and methods for use therewith.

BACKGROUND

In pacemakers that are configured to pace an atrial cardiac chamber, detection of an atrial evoked response (AER), in response to delivery of an atrial pacing pulse, is of great value. The presence of an atrial evoked response is indicative of an atrial pacing pulse causing atrial capture. In a pacemaker that is capable of performing "atrial autocapture," the pacemaker may automatically and gradually reduce an atrial stimulus amplitude to determine the stimulus amplitude at which atrial capture is lost, which provides an estimate for an atrial capture threshold. Once a pacemaker determines the atrial capture threshold, the pacemaker can automatically set the atrial stimulus amplitude to be equal to the atrial capture threshold plus a small safety margin. Providing atrial autocapture is very valuable because the atrial stimuli safety margin may be minimized, which reduces battery current drain and thereby prolongs pacemaker longevity. This is especially critical for leadless pacemakers, because the battery takes up most of the volume of leadless pacemakers, and small size is important for leadless pacemakers, especially those that are implanted transvenously and left to reside inside the heart.

Atrial autocapture depends on atrial evoked response detection, but atrial evoked response detection is not a trivial endeavor. Atrial evoked response detection is challenging because of the small amplitude of a typical atrial evoked response. Indeed, a typical atrial evoked response is within the range of only about 1.0 millivolts (mV) to about 3.5 mV in amplitude, and typically has a duration of about 50 milliseconds or less.

When a pacing pulse is delivered, current is passed through a cathode electrode (e.g., a tip electrode of a leadless pacemaker) to an anode electrode (e.g., a ring or battery case electrode of the leadless pacemaker), and an electrode-to-electrolyte interface behaves like a capacitor and charges up to tens or hundreds of millivolts. After the pacing pulse is turned off and an active discharge is turned off, there is residual charge left on the electrode-to-electrolyte interface that creates a decaying potential between the electrodes. In a leadless pacemaker, both the battery case electrode and the tip electrode charge up, leaving behind a decaying polarization potential that superimposes on the atrial evoked response. This polarization potential is often sufficiently large that the atrial evoked response is dwarfed and thereby totally obscured by the polarization potential.

Furthermore, an atrial evoked response typically includes a very early initial negative deflection that occurs within only a few milliseconds of the cathodic pacing pulse. Capturing the initial leading-edge may help to achieve the maximum deflection of the entire evoked response, thus enhancing evoked response detection. However, the active discharge of the output capacitor (also known as the pacing capacitor) typically takes place for about 7 to 10 milliseconds following the end of the pacing pulse. The active discharge process therefore superimposes on the early negative atrial evoked response, which obscures the atrial evoked response. Making the active discharge short enough (e.g., 3 to 4 milliseconds following the end of the atrial pacing pulse) to detect the full atrial evoked response is possible, but has negative consequences. On the helpful side, the active discharge cancels electrode polarization. However, when the active discharge is too short, 3 to 4 milliseconds of polarization is not adequately cancelled, resulting in the atrial evoked response being concealed by the electrode polarization. Additionally, excess atrial electrode polarization can lead to lack of ventricular pacing support caused by crosstalk in a ventricular sensing channel, potentially inhibiting ventricular pacing. Crosstalk mitigation may necessitate ventricular safety pacing, also known as committed ventricular pacing, which wastes battery current and thereby shortens the longevity of the ventricular pacemaker.

Various techniques have been developed to attempt to mitigate electrode polarization, and thereby improve atrial evoked response detection. For example, coating the electrodes with titanium nitride (TiN), ilridium oxide (IrOx), or platinum black, or combinations thereof, dramatically reduces electrode polarization. Indeed, pacemaker designers have used these coatings on pacemaker electrodes to reduce electrode polarization and thereby improve evoked response detection and even improve stimulation thresholds and efficiency.

Further, various techniques have been developed to improve the detection of an atrial evoked response in the presence of electrode polarization. For example, rather than simply comparing amplitudes of a portion of a sensed cardiac signal to an amplitude threshold, the portion of the sensed cardiac signal can be digitized and summed to extract an atrial evoked response integral that is compared to an integral threshold. If the atrial evoked response integral exceeds the integral threshold, then the pacemaker detects an atrial evoked response. However, such an integral technique does not work where an atrial evoked response is of sufficiently small amplitude that it remains obscured by electrode polarization after-potentials. Even more complex techniques have also been developed. For example, in one technique, about twenty digitized samples of a portion of a sensed cardiac signal are obtained and then correlated with a stored template for an atrial evoked response. Pearson's correlation coefficient may be used, but is very mathematically intensive requiring many multiplications. Alternatively, Kendell's tau correlation can be used to test the relationship between the template and the evoked response, wherein Kendell's tau correlation does not multiply, but rather, sorts and compares sample amplitudes. Unfortunately, frequently executed correlations (whether it is Pearson's or even Kendell's tau) is a significant burden on processor duty cycle and battery current drain. Preferably, a simpler process, such as differentiation of the atrial evoked response by performing twenty or fewer subtractions would be a better approach. The use of such a differentiation technique that relies on subtractions have been proven to be very effective for detecting a ventricular evoked response, each is typically about 3 to 4 time larger in amplitude than an atrial evoke response. However, because an atrial evoked response often has a very small amplitude, the use of such a differentiation technique that relies on subtractions is not always effective for detecting an atrial evoked response.

As can be appreciated from the above discussion, it would be beneficial if further techniques were available for reducing electrode polarizations, and more generally, improving detections of evoked responses, especially atrial evoked responses.

SUMMARY

Embodiments of the present technology described herein are directed to implantable medical devices (IMDs), and methods for used therewith. In certain embodiments, such an IMD includes a pacing capacitor and a sensing circuit. The IMD can also include anode and cathode electrodes, if the IMD is a leadless pacemaker that is configured to be implanted in or on a cardiac chamber. Alternatively, if the IMD is a more conventional type of pacemaker, the IMD can be electrically coupled to anode and cathode electrodes located on a cardiac lead that extends from the IMD. Regardless of the specific type of IMD, the IMD can also include one or more voltage generators configured to produce a plurality of different voltages including a first voltage and a second voltage, the second voltage having a greater magnitude than the first voltage. Additionally, the IMD can include a controller configured to control when the pacing capacitor is being charged using the first voltage, when the pacing capacitor is being charged using the second voltage, and when the pacing capacitor is being discharged to deliver a pacing pulse between the anode and cathode electrodes of, or electrically coupled to, the IMD.

The sensing circuit of the IMD can be configured to sense a cardiac electrical signal, which may be sensed following a blanking period that follows the delivery of a pacing pulse. The IMD can also include an evoked response detector configured to determine, based on a portion of the cardiac electrical signal sensed by the sensing circuit following delivery of the pacing pulse (as well as following the blanking period), and following a charge period, whether an evoked response occurred in response to the pacing pulse.

In accordance with certain embodiments of the present technology, the controller of the IMD is configured to cause the pacing capacitor to be charged using the second voltage during a portion of the charge period, and to cause the pacing capacitor to be charged using the first voltage during another portion of the charge period. In such an embodiment, the charge period, which is a period during which the pacing capacitor is charged following delivery of the pacing pulse, begins following the pacing pulse being delivered and ends prior to the evoked response detector being used to determine whether the evoked response occurred in response to the pacing pulse.

In accordance with certain embodiments of the present technology, the evoked response detector (ERD), or a portion thereof, can be implemented by the controller. Accordingly, it is also possible the ERD is implemented completely separate from controller, using circuitry that is dedicated to determining whether an evoked response occurred in response to a pacing pulse.

In accordance with certain embodiments of the present technology, the controller is configured to cause: the pacing capacitor to be charged using the first voltage, during a first period of time; the pacing pulse to be delivered between the anode and cathode electrodes by at least partially discharging the pacing capacitor, during a second period of time, that follows the pacing capacitor being charged using the first voltage during the first period of time; the pacing capacitor to be charged using the second voltage that is greater in magnitude than the first voltage, during a third period of time, that follows the pacing pulse being delivered during the second period of time; and the pacing capacitor to be charged using the first voltage that is smaller in magnitude than the second voltage, during a fourth period of time, that follows the pacing capacitor being charged using the second voltage during the third period of time. In certain such embodiments, the evoked response detector is configured to determine, during a fifth period of time, that follows the pacing capacitor being charged using the first voltage during the fourth period of time, whether the evoked response occurred in response to the pacing pulse being delivered during the second period of time.

In accordance with certain embodiments of the present technology, the one or more voltage generators of the IMD include a first voltage generator that produces the first voltage, and a second voltage generator that produces a further voltage that is selectively added to the first voltage to produce the second voltage. In certain such embodiments, the controller controls when the further voltage is selectively added to the first voltage to produce the second voltage.

In accordance with other embodiments of the present technology, the one or more voltage generators of the IMD include an amplifier that selectively receives one of a first analog signal or a second analog signal from a digital-to-analog converter (DAC). The amplifier is configured to output the first voltage in response to receiving the first analog signal from the DAC, and configured to output the second voltage in response to receiving the second analog signal from the DAC. In certain such embodiments, the controller is configured to selectively provide a first digital signal to the DAC to cause the first analog signal to be output by the DAC, and selectively provide a second digital signal to the DAC to thereby cause the second analog signal to be output by the DAC.

In accordance with further embodiments of the present technology, the one or more voltage generators include a voltage generator that produces the second voltage, and a diode including an anode terminal that receives the second voltage and a cathode terminal the outputs the first voltage. In certain such embodiments, the controller is configured to control when second voltage received by the anode terminal of the diode is used to charge the pacing capacitor, and when the first voltage output at the cathode terminal of the diode is used to charge the pacing capacitor.

A method, according to an embodiments of the present technology, includes during a first period of time, charging the pacing capacitor using a first voltage. The method also includes during a second period of time, that follows the pacing capacitor being charged using the first voltage during the first period of time, delivering a pacing pulse between the anode and cathode electrodes by at least partially discharging the pacing capacitor. The method further includes during a third period of time, that follows the pacing pulse being delivered during the second period of time, charging the pacing capacitor using a second voltage that is greater in magnitude than the first voltage. Additionally, the method includes during a fourth period of time, that follows the pacing capacitor being charged using the second voltage during the third period of time, charging the pacing capacitor using the first voltage that is smaller in magnitude than the second voltage. Further, the method includes during a fifth period of time, that follows the pacing capacitor being charged using the first voltage during the fourth period of time, using the sensing circuit to sense a cardiac electrical signal, and determining therefrom whether an evoked response occurred in response to the pacing pulse being delivered during the second period of time. The above summarized steps can be repeated each time another pacing pulse is to be delivered.

In accordance with certain embodiments of the present technology, the third period of time, during which the pacing capacitor is charged using the second voltage, and fourth period of time, during which the pacing capacitor is charged using the first voltage, both occur during a blanking period of the sensing circuit. In such embodiments, the fifth period of time, during which the sensing circuit is used to sense the cardiac electrical signal, and during which and during which the evoked response detector determines whether the evoked response occurred, follows the blanking period.

Beneficially, the charging the pacing capacitor during the third period of time using the second voltage, that is greater in magnitude than the first voltage, reduces a magnitude of a polarization artifact superimposed on the evoked response within the cardiac electrical signal, sensed using the sensing circuit, compared to if the pacing capacitor were instead charged using the first voltage during the third period of time.

In accordance with certain embodiments of the present technology, the first voltage comprises a specified pacing voltage, and the second voltage is within a range of 5% to 30% greater in magnitude than the specified pacing voltage.

In accordance with certain embodiments of the present technology, the third and the fourth periods of time are portions of a charge period during which the pacing capacitor is charged, following the delivering the pacing pulse during the second period of time, wherein a duration of the third period of time is between 10% and 90% of the charge period.

In accordance with certain embodiments of the present technology, the cardiac chamber, to which the pacing pulse is delivered, comprises an atrial cardiac chamber, and the evoked response comprises an atrial evoked response. Alternatively, the cardiac chamber, to which the pacing pulse is delivered, comprises a ventricular cardiac chamber, and the evoked response comprises a ventricular evoked response.

In accordance with certain embodiments of the present technology, the method further comprises, following delivery of the pacing pulse, using feedback to adjust a duration of the third period of time, during which the pacing capacitor is charged using the second voltage, to thereby reduce, minimize or eliminate a polarization artifact superimposed on the evoked response within the cardiac electrical signal sensed using the sensing circuit. Alternatively, or additionally, the method can comprise, following delivery of the pacing pulse, using feedback to adjust a magnitude of the second voltage that is used to charge the pacing capacitor during a said third period of time, to thereby reduce, minimize or eliminate a polarization artifact superimposed on the evoked response within the cardiac electrical signal sensed using the sensing circuit.

A method, according to certain embodiments of the present technology, is for use by an implantable medical device (IMD) including a pacing capacitor and a sensing circuit, and also including or electrically coupled to anode and cathode electrodes. The method includes charging the pacing capacitor to a first voltage, and while the pacing capacitor is charged to the first voltage, delivering a pacing pulse between the anode and cathode electrodes by at least partially discharging the pacing capacitor. The method also includes following delivery of the pacing pulse, charging the pacing capacitor using a second voltage during a portion of a charge period, and charging the pacing capacitor using the first voltage during another portion of the charge period, wherein the second voltage is greater in magnitude than the first voltage. In such embodiments, the charge period, which is a period during which the pacing capacitor is charged following delivery of the pacing pulse, begins following the pacing pulse being delivered and ends prior to circuitry of the IMD being used for determining whether an evoked response occurred in response to the pacing pulse being delivered. The method can also include, following the charge period, using the circuitry of the IMD to determine whether the evoked response occurred in response to the pacing pulse being delivered.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF DRAWINGS

Embodiments of the present technology relating to both structure and method of operation may best be understood by referring to the following description and accompanying drawings, in which similar reference characters denote similar elements throughout the several views:

FIG. 10 is a high level flow diagram that is used to summarize methods according to various embodiments of the present technology.

DETAILED DESCRIPTION

Figures 1, 2, 3:
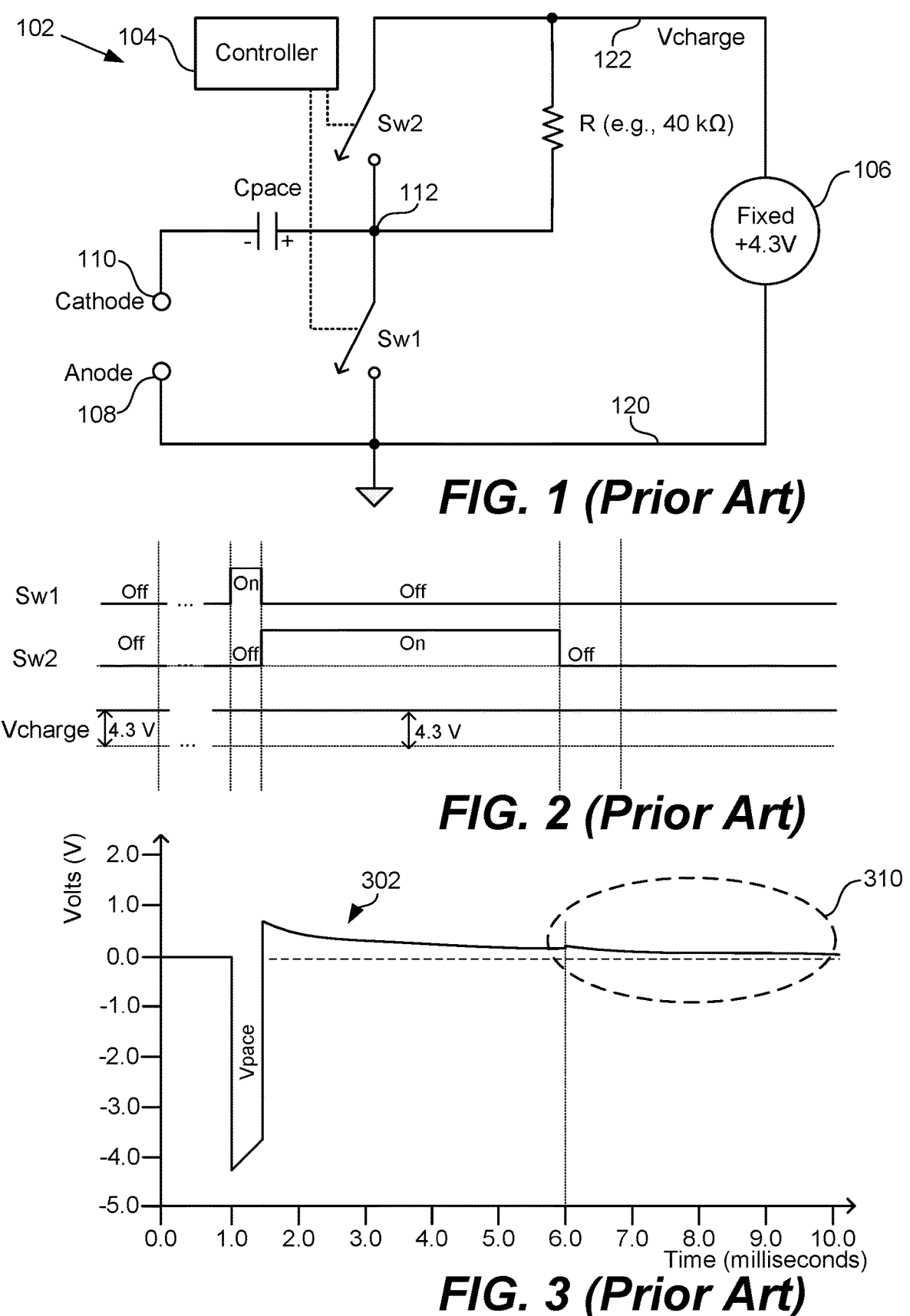
FIG. 1 shows an example circuit of an IMD including a pacing capacitor used to deliver a pacing pulse between anode and cathode electrodes of, or electrically coupled to, the IMD.
FIG. 2 is a timing diagram used to describe operation of the circuit shown in FIG. 1, including discharging and recharging of the pacing capacitor.
FIG. 3 is a voltage waveform diagram used to describe the delivery of a pacing pulse, using the circuit shown in FIG. 1, and to describe an electrode polarization that may adversely affect the IMD's ability to detect an evoked response to the pacing pulse following the recharging of the pacing capacitor.

FIG. 1 is a high level diagram that is used to describe an example circuit 102 of an IMD that can be used to deliver a pacing pulse between anode and cathode electrodes. Where the circuit 102 is included in a leadless pacemaker type of IMD, the anode and cathode electrodes can be parts of the leadless pacemaker. Alternatively, where the circuit 102 is included in a more conventional pacemaker that includes or is coupled to one or more cardiac leads, the anode and cathode electrodes can be located on a cardiac lead that is electrically coupled to the pacemaker.

Referring to FIG. 1, the circuit 102 is shown as including a pacing capacitor Cpace, a controller 104, a voltage generator 106, switches Sw1 and Sw2, and a resistor R. Also shown in FIG. 1 are an anode electrode 108 and a cathode electrode 110. The voltage generator 106 is coupled between a low voltage rail 120 and a high voltage rail 122. In FIG. 1, the low voltage rail 120 is shown as being coupled to ground. However, in other embodiments, the low voltage rail 120 need not be coupled to ground, so long as the low voltage rail has a lower voltage potential than the high voltage rail 122. The switch Sw1 can also be referred to as a pacing switch, or Sw_pace, since it is used to selectively deliver a pacing pulse between the anode and cathode electrode 108, 110. The switch Sw2 can also be referred to as a charge switch, or Sw_charge, since it is used for selectively charging the pacing capacitor Cpace, wherein charging includes recharging.

In FIG. 1, the voltage generator 106 is shown as outputting a fixed voltage of +4.3 volts (V). However, it is noted that a fixed voltage other than +4.3 V can be output by the voltage generator 106. Further, it is also possible that the voltage generator 106 can be an adjustable voltage generator, wherein the output of the voltage generator 106 is adjusted based on a capture threshold, so that the output of the voltage generator 106 is equal to the capture threshold plus a small safety margin.

Still referring to FIG. 1, the switch Sw1 is coupled between a node 112 and the low voltage rail 120, and the switch Sw2 is coupled between the node 112 and the high voltage rail. The pacing capacitor Cpace is coupled between the node 112 and the cathode electrode 110. More particularly, one terminal of the capacitor (which can be referred to as the positive terminal) is coupled to the node 112, and the other terminal of the capacitor (which can be referred to as the negative terminal) is coupled to the cathode electrode 110.

The anode electrode 108 is coupled to the low voltage rail 120. The resistor R is coupled between the high voltage rail 122 and the node 112. Since the voltage and the current at the node 112 is used to either charge or discharge the pacing capacitor Cpace, the node 112 can also be referred to herein more particularly as the charge and discharge node 112. The resistor R provides for passive charging of the pacing capacitor Cpace. The switch Sw2 provides for active charging of the pacing capacitor, as will be described in more detail below.

Operation of the circuit 102 in FIG. 1 will now be described with reference to the timing diagram of FIG. 2, and the voltage waveform diagram of FIG. 3. The timing diagram of FIG. 2 shows when the switches Sw1 and Sw2 are turned on and off. The turning on of a switch can also be referred to as closing the switch; and the turning off of a switch can also be referred to as opening the switch. The timing diagram of FIG. 2 also shows that the voltage on the high voltage rail 122, which voltage can be referred to as Vcharge, remains at the fixed voltage, which is +4.3 V in this example. The voltage waveform 302 shown in FIG. 3 corresponds to the voltage potential between the anode and cathode electrodes 108, 110.

Referring to FIG. 2, while the pacing capacitor Cpace is charged to +4.3 V, the switch Sw1 is shown as being closed at 1.0 milliseconds, for a duration of 0.5 milliseconds. As shown in FIG. 3, the closing of the switch Sw1: drives the positive side of the pacing capacitor Cpace (which is coupled to the node 112) to the voltage of the low voltage rail 120 (which is ground in this example); and drives the negative side of the pacing capacitor Cpace (which is coupled to the cathode electrode 110) to −4.3 V. This causes charge to flow out of the pacing capacitor Cpace, driving current between the anode and cathode electrodes 108, 110 for 0.5 milliseconds and creating a negative pacing pulse (Vpace), as shown graphically in FIG. 3. The voltage at the cathode during the negative pacing pulse (Vpace) peaks at −4.3 V and then decays exponentially becoming less negative as charge is dumped out of the pacing capacitor Cpace. At the end of the pacing pulse, the switch Sw1 opens (i.e., is turned off), and the switch Sw2 closes (i.e., is turned on), thereby causing the pacing capacitor Cpace to recharge to +4.3 V for the duration that the switch Sw2 remains closed (i.e., remains turned on), which in this example, is 4.5 milliseconds (i.e., from 1.5 to 6.0 milliseconds).

Note that when the switch Sw1 opens (i.e., is turned off), and the switch Sw2 closes (i.e., is turned on), at 1.5 milliseconds, the voltage between the anode and cathode electrodes 108, 110, transitions from about −3.8 V to about +0.6 V, wherein the +0.6 V is due to a polarization potential on the electrodes. This polarization potential on the electrodes decays from about +0.6 V to about +0.2 V by the time the pacing capacitor Cpace is finished being recharged at 6.0 milliseconds. Note that even after the pacing capacitor Cpace is finished being recharged, a small but significant polarization potential slowly decays but remains at a level that can interfere with detecting an evoked response to the pacing pulse, as shown within the dashed oval 310. The small but significant polarization potential, shown within the dashed oval 310, is also referred to herein as a post recharge potential or a polarization artifact. The post recharge potential can undesirably cause transients in a sensing amplifier (not shown in FIG. 1), when the sensing amplifier comes out of blanking (at the end of a blanking period), and begins sensing for an evoked response to the pacing pulse. Such a transient in the sensing amplifier can undesirably interfere with detecting of the evoked response to the pacing pulse. Explained another way, a polarization artifact superimposed on an evoked response within a sensed cardiac electrical signal can make it difficult for a pacemaker to detect the evoked response. This is especially the case where the evoked response is an atrial evoked response, which typically has a much lower magnitude than a ventricular evoked response.

Certain embodiments of the present technology, which are initial described below with reference to FIGS. 4, 5 and 6, can be used to reduce a magnitude of a polarization artifact superimposed on an evoked response within a cardiac elec-
trical signal, sensed using a sensing circuit, compared to if
the pacing capacitor were instead charged in the manner
described above with reference to FIGS. 1, 2 and 3. Such
embodiments of the present technology utilize what is
referred to herein as a "turbo boost voltage" for a portion of
the period during which a pacing capacitor is recharged
following the delivery of a pacing pulse. As will be appre-
ciated from the following discussion, the "turbo boost volt-
age" has the effect of reducing a magnitude of a polarization
artifact superimposed on an evoked response within a car-
diac electrical signal, sensed using a sensing circuit, com-
pared to if the "turbo boost voltage" was not used (and
rather, a constant recharge voltage was used to recharge the
pacing capacitor). In the above discussion of FIGS. 1, 2 and
3, a constant recharge voltage of +4.3 V was used to recharge
the pacing capacitor Cpace following the delivery of the
pacing pulse. Accordingly, embodiments of the present
technology provide for an improvement over the example
circuit 102 described above with reference to FIGS. 1, 2 and
3.

Figures 4, 5, 6:
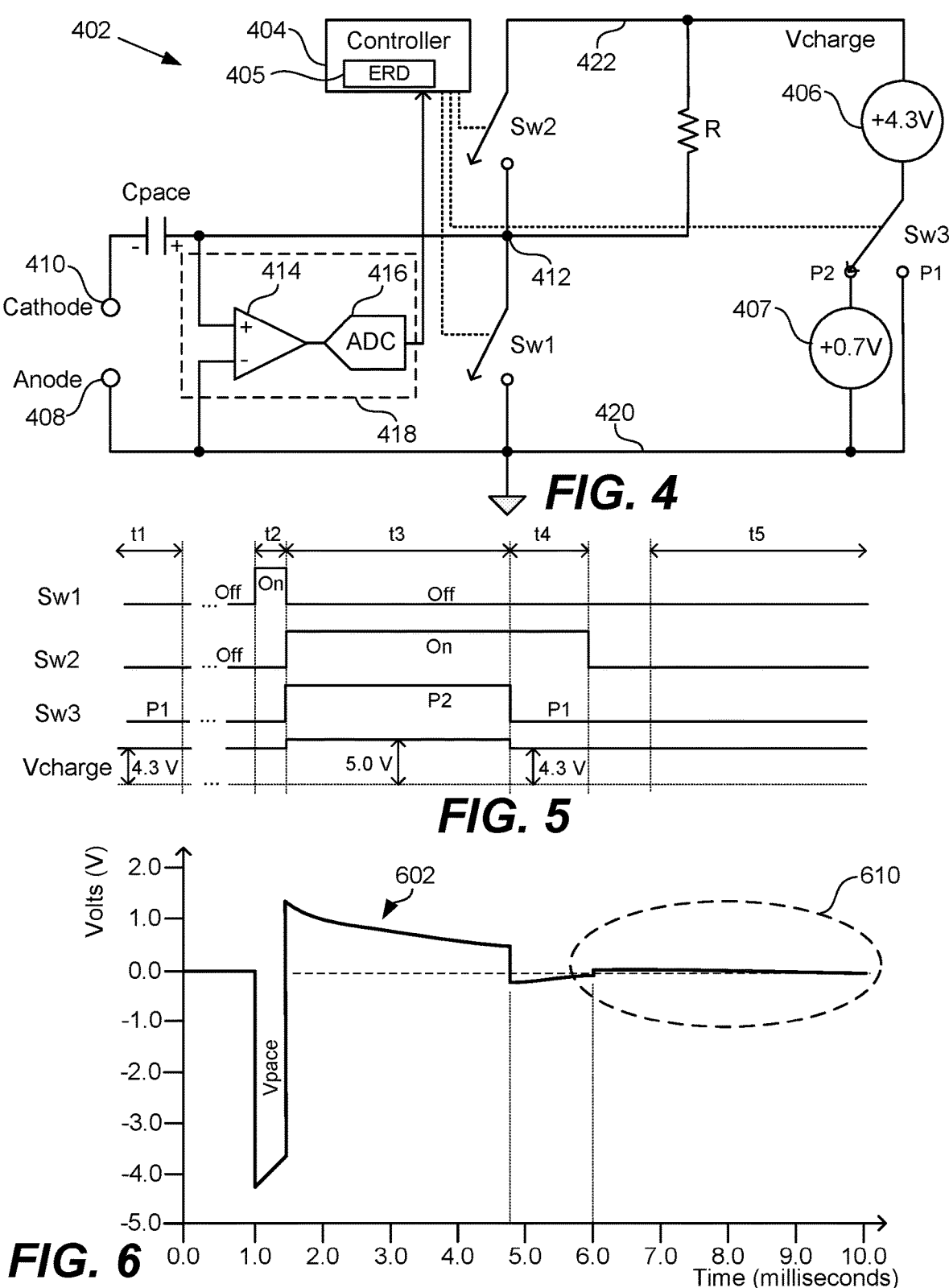
FIG. 4 shows a circuit of an IMD including a pacing capacitor used to deliver a pacing pulse between anode and cathode electrodes, in accordance with an embodiment of the present technology that reduces the electrode polarization following recharging of the pacing capacitor, and thereby improves the IMD's ability to detect an evoked response to the pacing pulse.
FIG. 5 is a timing diagram that is used to describe operation of the circuit shown in FIG. 4.
FIG. 6 is a voltage waveform diagram used to describe the delivery of a pacing pulse, using the circuit shown in FIG. 4, and to describe the reduction in the electrode polarization following recharging of the pacing capacitor, which improves the IMD's ability to detect an evoked response to the pacing pulse.

FIG. 4 is a high level diagram that is used to describe a
circuit 402 of an IMD that can be used to deliver a pacing
pulse between an anode electrode 408 and a cathode elec-
trode 410, in accordance with an embodiment of the present
technology. Where the circuit 402 is included in a leadless
pacemaker type of IMD, the anode and cathode electrodes
408, 410 can be parts of the leadless pacemaker. Alterna-
tively, where the circuit 402 is included in a more conven-
tional pacemaker that includes or is coupled to one or more
cardiac leads, the anode and cathode electrodes 408, 410 can
be located on a cardiac lead that is electrically coupled to the
pacemaker.

Still referring to FIG. 4, the circuit 402 is shown as also
including voltage generators 406 and 407, switches Sw1,
Sw2, and Sw3, a pacing capacitor Cpace, and a resistor R.
The circuit 402 also includes a controller 404, a sensing
amplifier 414, and an analog-to-digital converter (ADC)
416. The sensing amplifier 414 and the ADC 416 are an
example implementation of a sensing circuit 418 that senses
a voltage between the anode and cathode electrodes 408,
410. Additionally, the circuit 402 is shown as including an
evoked response detector (ERD) 405. In FIG. 4, the ERD
405 is shown as being part of the controller 404. However,
in alternative embodiments, a portion of the ERD 405, or an
entirety of the ERD 405, can be implemented by circuitry
other than the controller 404. The controller 404, which can
be implemented, e.g., using a microprocessor, a field pro-
grammable gate array (FPGA), or a state machine, can be
used to control the switches Sw1, Sw2 and Sw3. Accord-
ingly, it should be appreciated that the controller 404 can
control the charging of the pacing capacitor Cpace (includ-
ing the use of the "turbo boost voltage") and the discharging
of the pacing capacitor Cpace, and thereby the delivery of
pacing pulses. The ERD 405, which can be implemented,
e.g., using a microprocessor, an FPGA, or a state machine,
but is not limited thereto. In FIG. 4, the low voltage rail 420
is shown as being coupled to ground. However, in certain
embodiments, the low voltage rail 420 need not be coupled
to ground, so long as the low voltage rail has a lower voltage
potential than the high voltage rail 422.

The voltage generator 406 can include, e.g., a battery and
circuitry that is used to step-up or step-down a voltage
output by the battery to a specified level, as is known in the
art. The circuitry that is used to step-up or step-down the
voltage output by a battery to a specified level can be or
include, e.g., a DC-DC converter, such as a charge pump, a boost-converter or a buck-converter, but it not limited
thereto. Other voltage generators described herein (e.g., 106,
407, 806, 906, etc.) can be implemented in a similar manner,
or a different manner, depending upon the specific imple-
mentation.

The switch Sw1 can also be referred to as a pacing switch,
or Sw_pace, since it is used to selectively deliver a pacing
pulse between the anode and cathode electrodes 408, 410.
The switch Sw2 can also be referred to as a charge switch,
or Sw_charge, since it is used for selectively charging the
pacing capacitor Cpace, wherein charging includes recharg-
ing. The switch Sw3 is used to control whether Vcharge is
equal to the voltage output by the voltage generator 406, or
is equal to the sum of the voltages output by both of the
voltage generators 406. In this manner, the switch Sw3,
which is controlled by the controller 404, is used to control
timing of the "turbo boost voltage," as will be described in
additional detail below. Vcharge is the voltage that is used
to charge the pacing capacitor Cpace.

In FIG. 4, the voltage generator 406 is shown as output-
ting a fixed voltage of +4.3 V, and the voltage generator 407
is shown as outputting a fixed voltage of +0.7 V. Accord-
ingly, in the embodiment of FIG. 4, the switch Sw3 controls
whether Vcharge is +4.3 V or +5.0 V. More specifically,
when the switch Sw3 is connected to a first pole (P1),
Vcharge will be equal to +4.3 V; and when the switch Sw3
is connected to a second pole (P2), Vcharge will be equal to
4.3 V+0.7 V=+5.0 V. This is because when the Sw3 is
connected to the second pole (P2), the voltage generators
406 and 407 are connected in series between the low and
high voltage rails 420, 422. It is noted that a fixed voltage
other than +4.3 V can be output by the voltage generator
406, and a fixed voltage other than +0.7 V can be output by
the voltage generator 407. Further, it is also possible that one
or more of the voltage generators 406, 407 can be a variable
voltage generator, wherein the output(s) of one or more of
the voltage generator(s) is/are adjustable based on a capture
threshold. For example, in certain embodiments, the voltage
generator 406 can be controlled to output a voltage equal to
a capture threshold pulse a small safety margin. The voltage
generators 406 and 407 can share a common battery, but can
include separate circuitry to achieve two different desired
voltage levels, such as +4.3 V and +0.7 V, but is not limited
thereto.

Still referring to FIG. 4, the switch Sw1 is coupled
between a node 412 and the low voltage rail 420, and the
switch Sw2 is coupled between the node 412 and the high
voltage rail 422. The pacing capacitor Cpace is coupled
between the node 412 and the cathode electrode 410. The
anode electrode 408 is coupled to the low voltage rail 420.
The resistor R is coupled between the high voltage rail 422
and the node 412. Since the voltage and the current at the
node 412 is used to either charge or discharge the pacing
capacitor Cpace, the node 412 can also be referred to herein
more particularly as the charge and discharge node 412. As
was also the case in the circuit 102 in FIG. 1, the resistor R
is used for passive charging of the pacing capacitor Cpace,
and the switch Sw2 is used for active charging of the pacing
capacitor Cpace. The passive charging of the pacing capaci-
tor Cpace, through the resistor R, occurs while the switch
Sw2 is open, and provides a means of fully establishing a
desired pacing voltage level (e.g., of 4.3 V) on the pacing
capacitor Cpace. Presuming, for an example, that the capaci-
tance of the pacing capacitor is 4.7 microfarads (uF), and the
resistance of the resistor R is 40 kiloohms (kΩ), then the
time constant for the passively charging the pacing capacitor
Cpace, through the resistor R, is 4.7 uF*40 kΩ=188 milliseconds. Accordingly, over a pacing cycle period within the range of about 330 to 1333 milliseconds, there are several of such time constants available to fully charge the pacing capacitor Cpace to the desired voltage level, e.g., of 4.3 V.

Operation of the circuit 402 in FIG. 4 will now be described with reference to the timing diagram of FIG. 5, and the voltage waveform diagram of FIG. 6. The timing diagram of FIG. 5 shows when the switches Sw1 and Sw2 are turned on and off, and when the switch Sw3 is switched between first and second poles P1, P2. The timing diagram of FIG. 5 also shows when the voltage on the high voltage rail 422, which voltage can be referred to as Vcharge, transitions between +4.3 V and +5.0, or more generally, transitions between a nominal voltage level and the "turbo boost voltage" level. The nominal voltage level is the voltage at which a pacing pulse is to be delivered. The nominal voltage level can be a predetermined fixed voltage, or can be equal to a capture threshold plus a safety margin, but is not limited thereto. The voltage waveform 602 shown in FIG. 6 corresponds to the voltage potential between the anode and cathode electrodes 408, 410.

As noted above, the sensing amplifier 414 and the ADC 416 are an example implementation of a sensing circuit 418 that senses a voltage between the anode and cathode electrodes 408, 410. The non-inverting (+) input of the amplifier 414 is coupled to the positive terminal of the pacing capacitor (Cpace), and the inverting (−) input of the amplifier 414 is coupled to the low voltage rail 420, which in FIG. 4 is ground. Following a blanking period, which can be achieved in a manner described below, the output of the sensing amplifier 414 is indicative of a cardiac signal sensed between the anode and cathode electrode 408, 410. This sensed cardiac signal (e.g., an electrocardiogram), output by the sensing amplifier 414, is converted to a digital signal by the ADC 416 and provide to the ERD 405. In this manner, the ERD 405 is able to detect an evoked response to a pacing pulse, such as the pacing pulse (Vpace) described below with reference to FIG. 6. Various known and future developed techniques for detecting an evoked response can be used. For example, amplitudes of samples of the sensed cardiac signal following a blanking period can be compared to an appropriate threshold such that an evoked response is detected when the threshold is exceeded. Alternatively, multiple samples of the sensed signal following a blanking period can be summed, to essentially integrate the sensed cardiac signal for a period of time, and the sum can be compared to an appropriate threshold such that an evoked response is detected when the threshold is exceeded. It would also be possible to alternatively, or additionally, use template matching or some other type or correlation to detect an evoked response. Other variations are also possible, and within the scope of the embodiments described herein.

While not shown in FIG. 4, so as to not clutter the FIG., a blanking switch can be located between the non-inverting (+) input of the amplifier 414 and the positive terminal of the pacing capacitor (Cpace), and another blanking switch can be located between the inverting (−) input of the amplifier 414 and the anode electrode 408, wherein such blanking switches can be selectively opened to provide a blanking period for the sensing amplifier 414, and more generally, for the sensing circuit 418. Additionally, a DC blocking capacitor can be located between the non-inverting (+) input and the positive terminal of the pacing capacitor (Cpace), and another DC blocking capacitor can be located between the inverting (−) input of the amplifier 414 and the low voltage rail 420. A blocking switch, also not shown in FIG. 4, can be coupled between the non-inverting (+) input and the inverting (−) input of the sensing amplifier 414 to selectively short the inputs of the sensing amplifier 414 together to selectively provide for blocking periods. In addition to controlling the switches Sw1, Sw2 and Sw3, the controller 404 can also control the aforementioned blanking switches, to thereby control the timing and duration of blanking periods. The controller 404 can also control the aforementioned blocking switch, to thereby control blocking periods.

Referring to FIG. 5, while the switch Sw3 is coupled to the first pole P1, which causes the pacing capacitor Cpace to be charged to +4.3 V (or more generally, the nominal voltage level), the switch Sw1 is shown as being closed at 1.0 milliseconds, for a duration of 0.5 milliseconds. As shown in FIG. 5, the closing of the switch Sw1: drives the positive side of the pacing capacitor Cpace (which is coupled to the node 412) to the voltage of the low voltage rail 420 (which is ground in this example); and drives the negative side of the pacing capacitor Cpace (which is coupled to the cathode electrode 410) to −4.3 V. This causes charge to flow out of the pacing capacitor Cpace, driving current between the anode and cathode electrodes 408, 410 for 0.5 milliseconds and creating a negative pacing pulse (Vpace), as shown graphically in FIG. 6. The voltage at the cathode during the negative pacing pulse (Vpace) peaks at −4.3 V and then decays exponentially becoming less negative as charge is dumped out of the pacing capacitor Cpace. At the end of the pacing pulse, at 1.5 milliseconds, the switch Sw1 opens (i.e., is turned off), the switch Sw2 closes (i.e., is turned on), and the switch Sw3 transitions to being connected to the pole P2, thereby causing the pacing capacitor Cpace to initially recharge to +5.0 V (the "turbo boost voltage"). As shown in the timing diagram of FIG. 5, the switch Sw3 remains connected to the pole P2 for a duration of 3.2 milliseconds, until 4.7 milliseconds, before it transitions back to being connected to the pole P1. When the switch Sw3 transitions back to being connected to the pole P1, at 4.7 milliseconds, the switch Sw2 remains closed (i.e., remains turned on) for another 1.3 milliseconds, until 6.0 milliseconds. Notice in FIG. 6, that after recharging of the pacing capacitor Cpace is complete, at 6.0 milliseconds, the post recharge potential between the anode and cathode electrodes 408, 410 approaches 0.0 V, as shown within the dashed oval 610. This is because the "turbo boost voltage" substantially cancels the electrode polarization and restores the pacing voltage on the pacing capacitor Cpace. Explained another way, use of the "turbo boost voltage" substantially eliminates the polarization artifact superimposed on an evoked response within a sensed cardiac signal. This makes it easier for an evoked response to be detected by the ERD 405 within a sensed cardiac signal, obtained by the sensing circuit 418, especially where the evoked response is an atrial evoked response.

Figure 7:
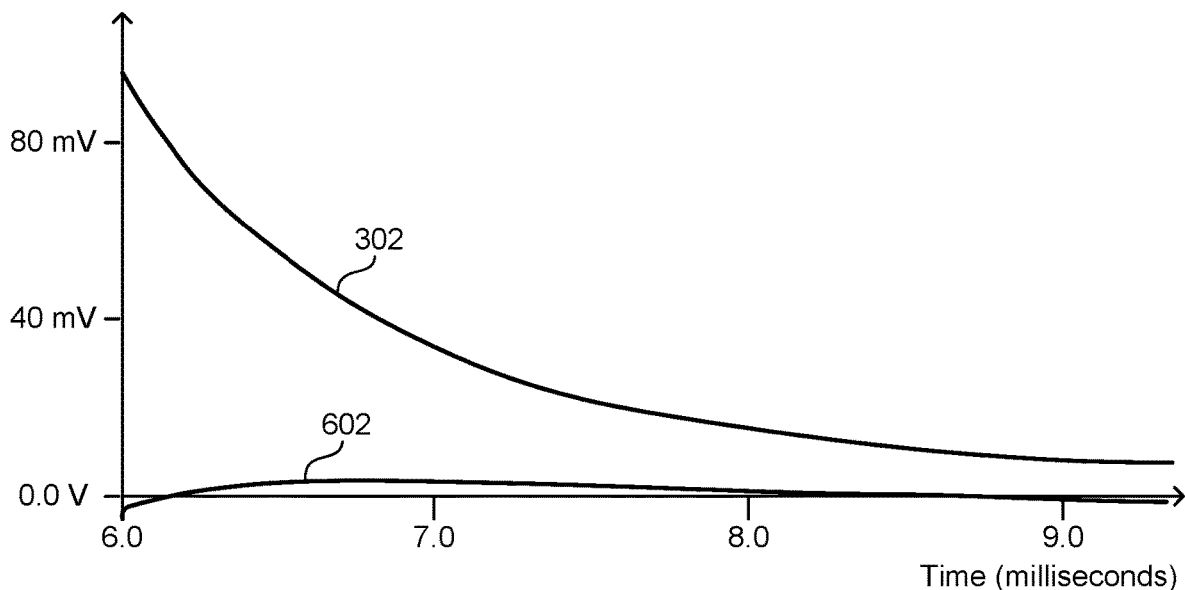
FIG. 7 includes and compares blown-up portions of the voltage waveforms initially shown in the dashed ovals in FIGS. 3 and 6.

Referring now to FIG. 7, shown therein is a blown-up portion of the regions within the dashed ovals 310 and 610, initially shown in FIGS. 3 and 6. More specifically, a blown-up portion of the voltage waveform 302 (initially shown in FIG. 3) and a blown-up portion of the voltage waveform 602 (initially shown in FIG. 6) are shown relative to one another in FIG. 7. As can be appreciated from FIG. 7, the electrode polarization is substantially smaller in the voltage waveform 602, following recharging of the pacing capacitor Cpace using the "turbo boost voltage", compared to the electrode polarization in the voltage waveform 302, when recharging was performed using a constant voltage without the "turbo boost voltage."

Referring back to FIGS. 3 and 6, it can be appreciated that that the pacing pulses delivered using the pacing capacitor Cpace are identical, but the recharges of the pacing capacitor Cpace are clearly different. More specifically, it could be appreciated from a comparison between the timing diagrams in FIGS. 2 and 5 that the "turbo boost voltage" provided for about +0.7 V of extra recharge voltage (above the nominal +4.3 V recharge voltage) for the first 3.2 milliseconds of the recharge. This use of the "turbo boost voltage" advantageously cancels the polarization more than the conventional recharge. As shown in FIG. 6, during the last 1.3 milliseconds of the recharge of the pacing capacitor Cpace, the charge (Vcharge) on the pacing capacitor Cpace is very close to the +4.3 V target pacing voltage, as was also the case when using the conventional recharge, as was shown in FIG. 3.

The post recharge regions of the voltage waveforms 302 and 602 are respectively shown within the dashed ovals 310 and 610, in FIGS. 3 and 6, which regions are blown-up in FIG. 7, as was explained above. The 3.2 milliseconds duration of the "turbo boost voltage," during which the +0.7 V was added to the nominal +4.3 V, was determined empirically. However, in other embodiments, the duration of the "turbo boost voltage," and more particularly, the duration that the extra voltage (above the desired nominal pacing voltage level) was used to recharge the pacing capacitor Cpace, can be determined using feedback and an algorithm performed by the controller 404 after the sensing amplifier 414 comes out of "blanking." Alternatively, or additionally, a magnitude of the "turbo boost voltage," and more particularly, the magnitude of the extra voltage (above the desired pacing voltage level) can be determined using feedback and an algorithm performed by the controller 404 after the sensing amplifier 414 comes out of "blanking."

Figure 8:
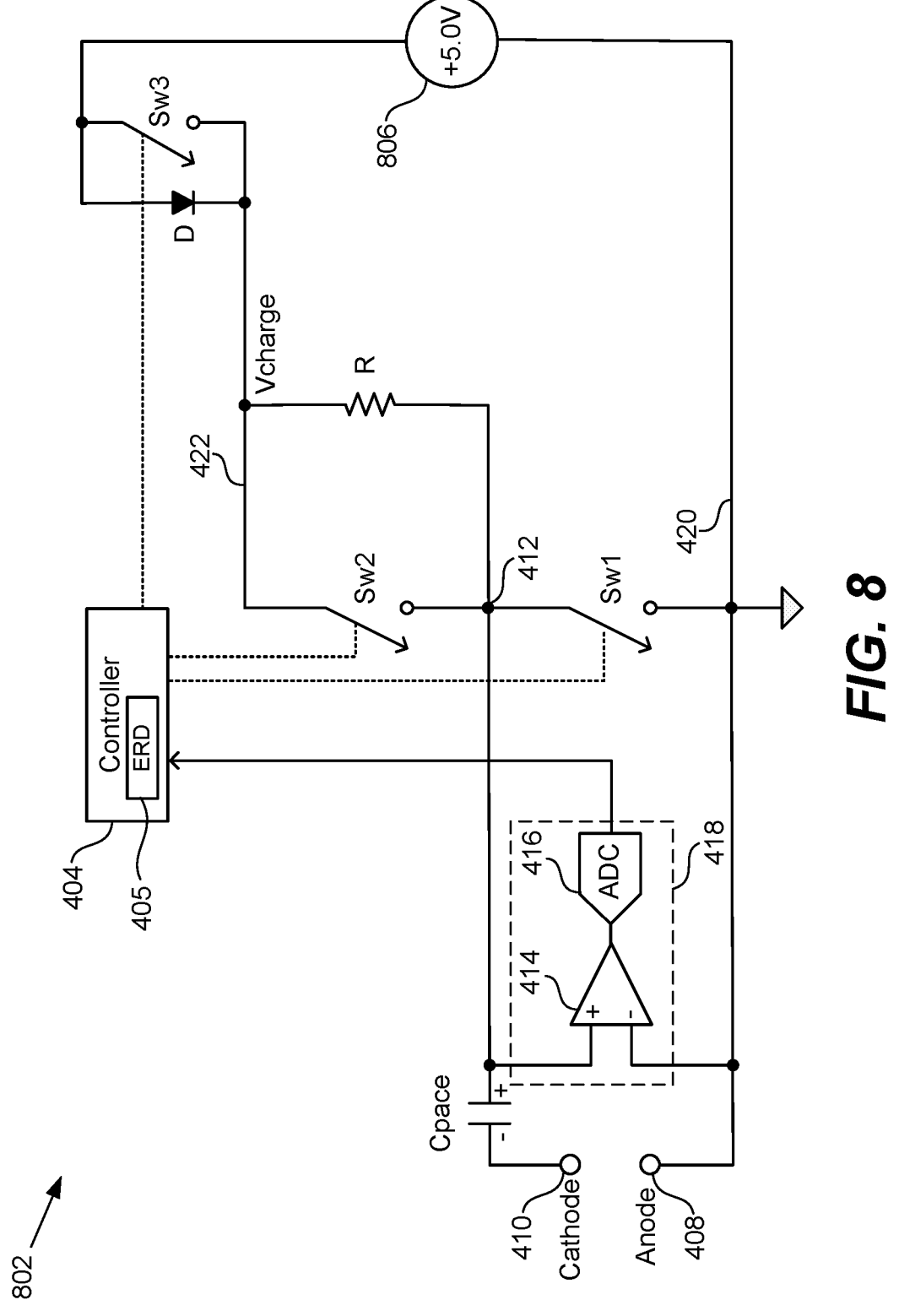
FIG. 8 shows a circuit of an IMD including a pacing capacitor used to deliver a pacing pulse between anode and cathode electrodes, in accordance with another embodiment of the present technology that reduces the electrode polarization following recharging of the pacing capacitor, and thereby improves the IMD's ability to detect an evoked response to the pacing pulse.
Figure 9:
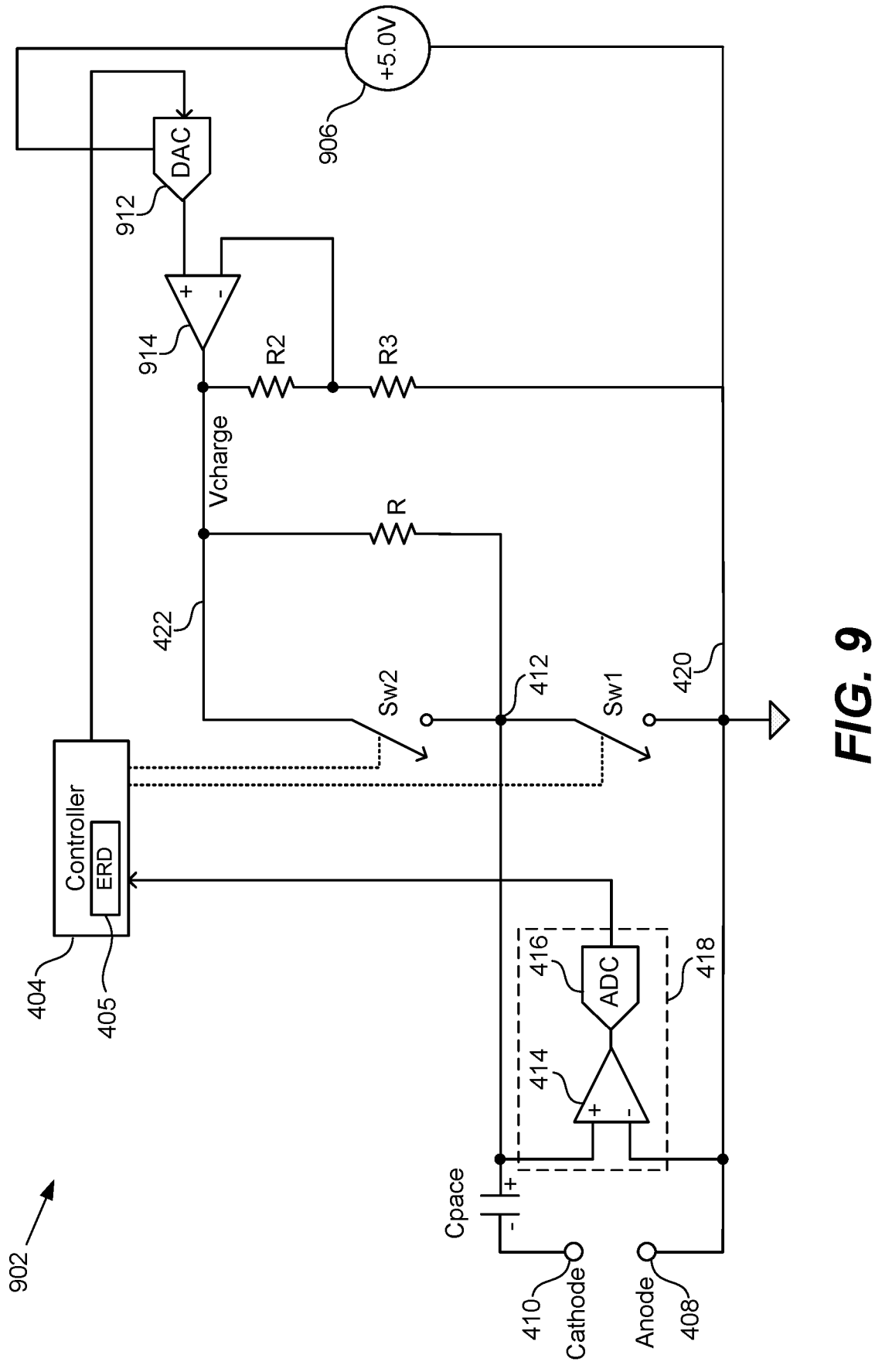
FIG. 9 shows a circuit of an IMD including a pacing capacitor used to deliver a pacing pulse between anode and cathode electrodes, in accordance with still another embodiment of the present technology that reduces the electrode polarization following recharging of the pacing capacitor, and thereby improves the IMD's ability to detect an evoked response to the pacing pulse.

In the circuit 402 shown in FIG. 4, the "turbo boost voltage" is essentially achieved using a step function that is implemented using the switch Sw3 and the additional voltage generator 407, which is used to add an additional voltage level of +0.7 V to the nominal voltage level of +4.3 V that is provided by the voltage generator 406. There are myriad of other techniques and circuits that can be used to selectively provide the "turbo boost voltage," some of which are described below with reference to FIGS. 8 and 9. In FIGS. 8 and 9, elements that are the same or similar to those described above with reference to FIG. 4 are numbered the same, and need not be described again.

The timing diagram shown in FIG. 5 and the voltage waveform shown in FIG. 6 also generally correspond to the operation the circuit 802 shown in FIG. 8, and the circuit 902 shown in FIG. 9. However, when the timing diagram in FIG. 5 is used to describe the operation of the circuit 802 in FIG. 8, it should be understood that the switch Sw3 in FIG. 8 should be closed (i.e., turned on) when switch Sw3 in FIG. 3 was connected to the pole P1, and the switch Sw3 in FIG. 8 should be opened (i.e., turned off) when the switch Sw3 in FIG. 3 was connected to the pole P2. More generally, in the embodiment of FIG. 8, Vcharge is equal to the nominal recharge voltage when the switch Sw3 is open, and Vcharge is equal to the "turbo boost voltage" when the switch Sw3 is closed.

Referring to FIG. 8, shown therein is a fixed voltage generator 806 shown as outputting +5.0 V. Also shown is a diode D connected in parallel with the switch Sw3 and in series with the switch Sw2. In the circuit 802, when the switch Sw3 is open, the switch Sw2 is closed, and the switch Sw1 is open, the Vcharge that is used to charge the pacing capacitor Cpace is equal to the +5.0 V (output by the voltage generator 806) minus a voltage drop of 0.7 V caused by the diode D, and thus, the Vcharge is equal to +4.3 V. In the embodiment of FIG. 8, the "turbo boost voltage" is achieved by closing the switch Sw3 (while the switch Sw2 is closed, and the switch Sw1 is open), which causes the diode D to be bypassed such that the Vcharge that is used to charge the pacing capacitor Cpace is equal to +5.0 V (output by the voltage generator 806).

Explained another way, in the embodiment described with reference to FIG. 8, the voltage generator 806 produces the "turbo boost voltage" (e.g., +5.0 V) that is provided to an anode terminal of the diode D, and a cathode terminal of the diode D outputs the nominal pacing voltage (e.g., +4.3 V). The controller 404, by controlling the switch Sw3, controls when the "turbo boost voltage" received by the anode terminal of the diode D is used to charge the pacing capacitor Cpace, and when the nominal pacing voltage output at the cathode terminal of the diode D is used to charge the pacing capacitor Cpace. In an embodiment, the voltage produced by the voltage generator 806 is equal to a capture threshold, plus a safety margin, plus 0.3 V.

In FIG. 9, the circuit 902 is shown as including a digital-to-analog converter (DAC) 912 followed by an amplifier 914, the output of which provides the Vcharge that is used to charge the pacing capacitor Cpace. The controller 404 provides a digital amplitude signal to the DAC 912, which converts the digital amplitude signal to an analog voltage signal, which is amplified to the Vcharge level by the amplifier 914. Accordingly, in this embodiment, the controller 404 controls the timing of when the "turbo boost voltage" is used, by controlling when the digital amplitude signal that corresponds to the increased charging voltage level (e.g., +5.0 V) is provided to the DAC 912, and when the nominal charging voltage level (e.g., +4.3 V) is used. Additionally, in the embodiment of FIG. 9, the controller 404 can precisely control the magnitude of the "turbo boost" by controlling the precise value of the digital amplitude signal that is provided to the DAC 912. In FIG. 9, the voltage generator 906 is shown as powering the DAC 912, and can also power other circuitry of the circuit 902. It would also be possible for one or more other voltage generators to be used to power the DAC 912 and other circuitry.

In summary, in accordance with certain embodiments of the present technology described herein, recharging of the pacing capacitor Cpace with a voltage greater than the nominal pacing voltage for a proportion of the recharge duration is used to reduce electrode polarization and achieve recharge to the desired pacing pulse voltage. The voltage greater than the nominal pacing voltage is often referred to herein as the "turbo boost voltage." The sensing circuit 418 can be used to measure the residual post recharge voltage induced artifact. In certain embodiments, a feedback system can be used to minimize the post recharge voltage induced artifact by adjusting the turbo boost voltage duration and/or magnitude.

The circuits 402, 802, and 902 described above with reference to FIGS. 4, 8 and 9, respectively, are just a few example implementation of circuits that can be used to selectively produce the "turbo boost voltage" and selectively transition between the "turbo boost voltage" and a nominal recharge voltage. One of skill in the art reading this disclosure will appreciate that various other circuits can be used while being within the scope of the embodiments described herein. The nominal recharge voltage, which can also be referred to as the nominal pacing voltage, can be a predetermined fixed voltage, or can be equal to a capture threshold plus a specified safety margin.

FIG. 10 is a high level flow diagram that is used to summarize methods according to various embodiments of the present technology. Such methods are for use by an IMD including a pacing capacitor (e.g., Cpace) and a sensing circuit (e.g., 418), and also including or electrically coupled to anode and cathode electrodes (e.g., 408 and 410). The IMD can be a leadless cardiac pacemaker that includes the anode and cathode electrodes. Alternatively, the IMD can be a more conventional type of pacemaker that is electrically coupled to the anode and cathode electrodes via one or more leads on which the electrodes are located. Other variations are also possible and within the scope of the embodiments described herein. Embodiments of the present technology are especially useful for detecting atrial evoked responses that occur in response to atrial pacing pulses being delivered to an atrial cardiac chamber. Additionally, embodiments of the present technology are also useful for detected ventricular evoked responses that occur in response to ventricular pacing pulses being delivered to a ventricular cardiac chamber, and are especially useful where the ventricular evoked responses are of relatively low magnitude. The methods described with reference to FIG. 10 are cyclical, and thus, the starting point for describing such methods (i.e., the entry point into the flow diagram of FIG. 10) is arbitrary.

Referring to FIG. 10, step 1001 involves, during a first period of time, charging the pacing capacitor using a first voltage (e.g., +4.3 V). Additional details of step 1001, according to certain embodiments of the present technology, are provided below. Step 1002 involves, during a second period of time (that follows the pacing capacitor being charged using the first voltage during the first period of time, at step 1001), delivering a pacing pulse between the anode and cathode electrodes by at least partially discharging the pacing capacitor. Step 1003 involves during a third period of time (that follows the pacing pulse being delivered during the second period of time, at step 1003), charging the pacing capacitor using a second voltage (e.g., +5.0 V) that is greater in magnitude than the first voltage. Step 1004 involves during a fourth period of time (that follows the pacing capacitor being charged using the second voltage, e.g., +5.0 V, during the third period of time, at step 1003), charging the pacing capacitor using the first voltage (e.g., +4.3 V) that is smaller in magnitude than the second voltage. Step 1005 involves during a fifth period of time (that follows the charging the pacing capacitor using the first voltage, e.g., +4.3 V, during the fourth period of time, at step 1004), using the sensing circuit (e.g., 418) to sense a cardiac electrical signal, and determining therefrom whether an evoked response occurred in response to the pacing pulse being delivered during the second period of time. The steps described with reference to FIG. 10 are repeated each time another pacing pulse is to be delivered, as can be appreciated from the arrowed line 1006 in FIG. 10. Accordingly, after an iteration of steps 1001, 1002, 1003, 1004 and 1005 is performed, another iteration of those steps is performed, and so on. Further, it is noted that a portion of the fifth period of time corresponding to an iteration of step 1005, can overlap with a portion of the first period of time corresponding to a next (i.e., immediately following) iteration of step 1001.

In certain embodiments, the charging of the pacing capacitor (e.g., Cpace in FIGS. 4, 8 and 9) using the first voltage, at step 1001, involves passive charging through a resistor (e.g., the resistor R in FIGS. 4, 8 and 9). The charge required to charge the pacing capacitor using the first voltage, at step 1001, may be relatively minimal, if most of the charge dumped from the pacing capacitor during an immediately preceding pacing cycle was already restored by an immediately preceding iteration of steps 1003 and 1004, using the second voltage and the first voltage, to drive current through the anode and cathode electrodes (e.g., 408, 410) into the pacing capacitor. In other words, charge restoration may be nearly complete following steps 1003 and 1004, because the time constant for a recharge process is relatively short. For example, presuming the lumped impedance between the anode and cathode electrodes is 0.5 kΩ, the time constant=4.7 uF*0.5 kΩ=2.35 milliseconds. Charge restoration may be nearly complete following a preceding iteration of steps 1003 and 1004 because the collective duration of steps 1003 and 1004 approaches two-time constants. Furthermore, use of the second voltage drives current into the pacing capacitor more vigorously during step 1003, than use of the first voltage drives current into the pacing capacitor during step 1004. Consequently, charging of the pacing capacitor using the first voltage, during an iteration of step 1001, may be regarded as "topping-off" the recharge process.

Referring briefly back to FIG. 5, the periods of time labeled t1, t2, t3, t4 and t5 in FIG. 5 are examples, respectively, of the first, second, third, fourth, and fifth periods of time referred to in the flow diagram of FIG. 10. Transitions from one of the first, second, third, fourth and fifth periods of time to another can be performed using switches (e.g., Sw1, Sw2 and Sw3) of the IMD that are controlled by a controller (e.g., 404) of the IMD. Referring briefly back to FIGS. 4 and 5, at step 1001, the charging of the pacing capacitor Cpace using the first voltage (e.g., +4.3 V), during the first period of time (t1), can be performing by passively charging the pacing capacitor Cpace, through the resistor R, while the switch Sw2 is open (i.e., turned off) and the switch Sw3 is connected to the pole P1. Further, it is noted that a portion t5 in FIG. 5, during a pacing cycle, can overlap with a portion of t1 in FIG. 5 that corresponds to a next (i.e., immediately following) pacing cycle.

It is noted that there may be a temporal gap between one or more of the aforementioned periods of time. For example, there can be (and likely is) a temporal gap between fourth period of time (t4) and the fifth period of time (t5), as is shown in the timing diagram of FIG. 5. This is just one example, which is not intended to be all encompassing.

In accordance with certain embodiments, the third period of time (during which the pacing capacitor is charged using the second voltage at step 1003), and fourth period of time (during which the pacing capacitor is charged using the first voltage at step 1004), both occur during a blanking period of the sensing circuit. The fifth period of time (during which the sensing circuit is used to sense the cardiac electrical signal, and during which the determining whether the evoked response occurred, at step 1005) follows the blanking period.

Step 1002 involves, during a second period of time (that follows the pacing capacitor being charged using the first voltage during the first period of time), delivering a pacing pulse between the anode and cathode electrodes by at least partially discharging the pacing capacitor. The cardiac chamber, to which the pacing pulse is delivered at step 1002, can be an atrial cardiac chamber. In such a case, the evoked response, for which there is a determination of whether it occurred at step 1005, is an atrial evoked response.

Alternatively, the cardiac chamber, to which the pacing pulse is delivered at step 1002, can be a ventricular cardiac chamber. In such a case, the evoked response, for which there is a determination of whether it occurred at step 1005, is a ventricular evoked response.

As can be appreciated from the above discussion of FIGS. 1-9, the charging the pacing capacitor during the third period of time (at step 1003) using the second voltage, that is greater in magnitude than the first voltage, reduces a magnitude of a polarization artifact superimposed on the evoked response within the cardiac electrical signal, sensed using the sensing circuit, compared to if the pacing capacitor were instead charged using the first voltage during the third period of time.

In accordance with certain embodiments of the present technology, the first voltage comprises a specified pacing voltage, and the second voltage (which is the "turbo boost voltage") is within a range of 5% to 30% greater in magnitude than the specified pacing voltage. For an example, if the first voltage is +4.3 V, than the second voltage can be within the range of +4.5 V to +5.6 V.

The third and the fourth periods of time (referred to at steps 1003 and 1004) are portions of a charge period during which the pacing capacitor is charged, following the delivering the pacing pulse during the second period of time (referred to at step 1002). In accordance with certain embodiments, a duration of the third period of time (during which the "turbo boost voltage" is used to charge the pacing capacitor) is between 10% and 90% of the charge period. For an example, if a charge period is 5.5 milliseconds, then the duration of the third period of time (during which the "turbo boost voltage" is used to charge the pacing capacitor) can be within the range of 0.5 milliseconds to 4.95 milliseconds. The second voltage (aka the "turbo boost voltage") can be used to charge (and more specifically, recharge) the pacing capacitor immediately following the delivery of the pacing pulse, before transitioning to using the first voltage (aka the pacing voltage) to charge the pacing capacitor, all of which occurs during a blanking period that coincides with a refractory period. In an alternative embodiment, following the delivery of the pacing pulse, the first voltage can be used to charge (and more specifically, recharge) the pacing capacitor immediately following the delivery of the pacing pulse, then the second voltage (aka the "turbo boost voltage") can be used for a period of time, before transitioning back to using the first voltage, all of which occurs during a blanking period that coincides with a refractory period.

In accordance with certain embodiments of the present technology, following delivery of a pacing pulse (at an instance of step 1003), feedback can be used to adjust a duration of the third period of time, during which the pacing capacitor is charged using the second voltage (aka the "turbo boost voltage"), to thereby reduce, minimize or eliminate a polarization artifact superimposed on the evoked response within the cardiac electrical signal sensed using the sensing circuit (e.g., 418). Additionally, or alternatively, such feedback can be used to adjust a magnitude of the second voltage (aka the "turbo boost voltage") that is used to charge the pacing capacitor during the third period of time, to thereby reduce, minimize or eliminate a polarization artifact superimposed on the evoked response within the cardiac electrical signal sensed using the sensing circuit.

Explained more generally, an IMD can use feedback to adjust the duration and/or the magnitude of the "turbo boost voltage" to reduce, and preferably eliminate or minimize, the polarization artifact superimposed on the evoked response within the cardiac electrical signal, sensed using the sensing circuit. In certain embodiments, such use of feedback to reduce, and preferably eliminate or minimize, a polarization artifact, can be performed periodically, e.g., once every 12 hours or 24 hours, or other period of time. Alternatively, or additionally, the use of feedback to reduce, and preferably eliminate or minimize, the polarization artifact, can be performed in response to a triggering event. Such a triggering event can be, for example, a detection of a change in a capture threshold (such as an arterial capture threshold, or a ventricular capture threshold) that causes a change to the first voltage, where the first voltage is equal to the capture threshold plus a safety margin. Such a use of feedback to reduce, and preferably eliminate or minimize, a polarization artifact, can be performed following delivery of a pacing pulse that is intended to cause an evoked response. Alternatively, such a use of feedback to reduce, and preferably eliminate or minimize, a polarization artifact, can be performed following delivery of a pacing pulse that is delivered during a refractory period, and thus, is not intended to cause an evoked response. Other variations are also possible and within the scope of the embodiments described herein.

Embodiments of the present technology described herein, which can be used to improve the detection of evoked responses to pacing pulses, can be used with other known and/or future developed techniques that reduce electrode polarization, to further improve the detection of evoked responses to pacing pulses. For an example, a cathodal electrode can be coated with TiN to reduce a polarization potential from about 1000 mV to about 100 mV. For another example, a platinum black coating can be added over a TiN base coating to further reduce the polarization potential of the cathodal electrode to about 20 to 35 mV, as described in U.S. patent application Ser. No. 17/199,260, titled "Biostimulator Having Low-Polarization Electrode(s)," to Bornzin et al., filed Mar. 11, 2021, which published as US2021/0308472, and is incorporated herein by reference. Additionally, or alternatively, a polarization potential of the anode electrode of a leadless pacemaker can be achieved by coating a docking button of the leadless pacing maker with TiN, which can reduce the polarization potential of the anode electrode to about 20 mV, as described in U.S. patent application Ser. No. 17/199,266, titled "Biostimulator Having Low-Polarization Electrode(s)," to Bornzin et al., filed Mar. 11, 2021, which published as US2021/0308466, and is incorporated by reference herein.

Embodiments of the present invention have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made.

For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An implantable medical device (IMD), comprising:
a pacing capacitor;
one or more voltage generators configured to produce a plurality of different voltages including a first voltage and a second voltage, the second voltage having a greater magnitude than the first voltage;
a controller configured to control when the pacing capacitor is being charged using the first voltage, when the pacing capacitor is being charged using the second voltage, and when the pacing capacitor is being discharged to deliver a pacing pulse between anode and cathode electrodes of, or electrically coupled to, the IMD;
a sensing circuit configured to sense a cardiac electrical signal; and
an evoked response detector configured to determine, based on a portion of the cardiac electrical signal sensed by the sensing circuit following delivery of the pacing pulse, and following a charge period, whether an evoked response occurred in response to the pacing pulse;
wherein the controller is configured to cause the pacing capacitor to be charged using the second voltage during a portion of the charge period, and to cause the pacing capacitor to be charged using the first voltage during another portion of the charge period;
wherein the charge period, which is a period during which the pacing capacitor is charged following delivery of the pacing pulse, begins following the pacing pulse being delivered and ends prior to the evoked response detector being used to determine whether the evoked response occurred in response to the pacing pulse; and
wherein the evoked response detector, or a portion thereof, can be implemented by the controller.

2. The IMD of claim 1, wherein the controller is configured to cause:
the pacing capacitor to be charged using the first voltage, during a first period of time;

the pacing pulse to be delivered between the anode and cathode electrodes by at least partially discharging the pacing capacitor, during a second period of time, that follows the pacing capacitor being charged using the first voltage during the first period of time;
the pacing capacitor to be charged using the second voltage that is greater in magnitude than the first voltage, during a third period of time, that follows the pacing pulse being delivered during the second period of time; and
the pacing capacitor to be charged using the first voltage that is smaller in magnitude than the second voltage, during a fourth period of time, that follows the pacing capacitor being charged using the second voltage during the third period of time; and
wherein the evoked response detector is configured to determine, during a fifth period of time, that follows the pacing capacitor being charged using the first voltage during the fourth period of time, whether the evoked response occurred in response to the pacing pulse being delivered during the second period of time.

3. The IMD of claim 2, wherein:
the third period of time, during which the pacing capacitor is charged using the second voltage, and the fourth period of time, during which the pacing capacitor is charged using the first voltage, both occur during a blanking period of the sensing circuit; and
the fifth period of time, during which the sensing circuit is used to sense the cardiac electrical signal, and during which the evoked response detector determines whether the evoked response occurred, follows the blanking period.

4. The IMD of claim 2, wherein the pacing capacitor being charged during the third period of time using the second voltage, that is greater in magnitude than the first voltage, reduces a magnitude of a polarization artifact superimposed on the evoked response within the cardiac electrical signal, sensed using the sensing circuit, compared to if the pacing capacitor were instead charged using the first voltage during the third period of time.

5. The IMD of claim 2, wherein:
the third and the fourth periods of time are portions of a charge period during which the pacing capacitor is charged, following the pacing pulse being delivered during the second period of time; and
wherein a duration of the third period of time is between 10% and 90% of the charge period.

6. The IMD of claim 2, further comprising switches that are controlled by the controller to cause transitions from one of the first, second, third, fourth and fifth periods of time to another.

7. The IMD of claim 1, wherein:
the first voltage comprises a specified pacing voltage; and
the second voltage is within a range of 5% to 30% greater in magnitude than the specified pacing voltage.

8. The IMD of claim 1, wherein:
the IMD comprises a leadless cardiac pacemaker that includes the anode and cathode electrodes.

9. The IMD of claim 1, wherein following delivery of the pacing pulse, the controller is configured to use feedback to adjust a duration of the portion of the charge period, during which the pacing capacitor is charged using the second voltage, to thereby reduce, minimize or eliminate a polarization artifact superimposed on the evoked response within the cardiac electrical signal sensed using the sensing circuit.

10. The IMD of claim 1, wherein following delivery of the pacing pulse, the controller is configured to use feedback to adjust a magnitude of the second voltage that is used to charge the pacing capacitor during the portion of the charge period, to thereby reduce, minimize or eliminate a polarization artifact superimposed on the evoked response within the cardiac electrical signal sensed using the sensing circuit.

11. The IMD of claim 1, wherein:
the one or more voltage generators include a first voltage generator that produces the first voltage, and a second voltage generator that produces a further voltage that is selectively added to the first voltage to produce the second voltage; and
the controller controls when the further voltage is selectively added to the first voltage to produce the second voltage.

12. The IMD of claim 1, wherein:
the one or more voltage generators include an amplifier that selectively receives one of a first analog signal or a second analog signal from a digital-to-analog converter (DAC);
the amplifier is configured to output the first voltage in response to receiving the first analog signal from the DAC, and configured to output the second voltage in response to receiving the second analog signal from the DAC; and
the controller is configured to selectively provide a first digital signal to the DAC to cause the first analog signal to be output by the DAC, and selectively provide a second digital signal to the DAC to thereby cause the second analog signal to be output by the DAC.

13. The IMD of claim 1, wherein:
the one or more voltage generators include a voltage generator that produces the second voltage, and a diode including an anode terminal that receives the second voltage and a cathode terminal that outputs the first voltage; and
the controller is configured to control when the second voltage received by the anode terminal of the diode is used to charge the pacing capacitor, and when the first voltage that is output at the cathode terminal of the diode is used to charge the pacing capacitor.

14. A method for use by implantable medical device (IMD) including a pacing capacitor, the method comprising:
producing a plurality of different voltages including a first voltage and a second voltage, the second voltage having a greater magnitude than the first voltage;
controlling when the pacing capacitor is being charged using the first voltage, when the pacing capacitor is being charged using the second voltage, and when the pacing capacitor is being discharged to deliver a pacing pulse between anode and cathode electrodes of, or electrically coupled to, the IMD;
sensing a cardiac electrical signal; and
determining, based on a portion of the cardiac electrical signal sensed following delivery of the pacing pulse, and following a charge period, whether an evoked response occurred in response to the pacing pulse;
wherein the controlling comprises causing the pacing capacitor to be charged using the second voltage during a portion of the charge period, and causing the pacing capacitor to be charged using the first voltage during another portion of the charge period; and
wherein the charge period, which is a period during which the pacing capacitor is charged following delivery of the pacing pulse, begins following the pacing pulse being delivered and ends prior to the determining whether the evoked response occurred in response to the pacing pulse.

15. The method of claim 14, wherein:
the controlling comprises:
causing the pacing capacitor to be charged using the first voltage, during a first period of time;
causing the pacing pulse to be delivered between the anode and cathode electrodes by at least partially discharging the pacing capacitor, during a second period of time that follows the pacing capacitor being charged using the first voltage during the first period of time;
causing the pacing capacitor to be charged using the second voltage that is greater in magnitude than the first voltage, during a third period of time that follows the pacing pulse being delivered during the second period of time; and
causing the pacing capacitor to be charged using the first voltage that is smaller in magnitude than the second voltage, during a fourth period of time that follows the pacing capacitor being charged using the second voltage during the third period of time; and
the determining, whether the evoked response occurred in response to the pacing pulse, is performed during a fifth period of time that follows the causing the pacing capacitor to be charged using the first voltage during the fourth period of time.

16. The method of claim 15, wherein:
the third period of time, during which the pacing capacitor is charged using the second voltage, and the fourth period of time, during which the pacing capacitor is charged using the first voltage, both occur during a blanking period of a sensing circuit of the IMD that is used to perform the sensing of the cardiac electrical signal; and
the fifth period of time, during which the sensing circuit of the IMD is used to perform at least a portion of the sensing of the cardiac electrical signal, and during which the determining whether the evoked response occurred, follows the blanking period.

17. The method of claim 15, wherein the pacing capacitor being charged during the third period of time using the second voltage, that is greater in magnitude than the first voltage, reduces a magnitude of a polarization artifact superimposed on the evoked response within the cardiac electrical signal, compared to if the pacing capacitor were instead charged using the first voltage during the third period of time.

18. The method of claim 15, wherein:
the third and the fourth periods of time are portions of a charge period during which the pacing capacitor is charged, following the pacing pulse being delivered during the second period of time; and
wherein a duration of the third period of time is between 10% and 90% of the charge period.

19. The method of claim 14, wherein:
the first voltage comprises a specified pacing voltage; and
the second voltage is within a range of 5% to 30% greater in magnitude than the specified pacing voltage.

20. The method of claim 14, wherein:
the IMD, with which the method is for use, with comprises a leadless cardiac pacemaker that includes the anode and cathode electrodes.

21. The method of claim 14, further comprising, following delivery of the pacing pulse, using feedback to adjust a duration of the portion of the charge period, during which the pacing capacitor is charged using the second voltage, to thereby reduce, minimize or eliminate a polarization artifact superimposed on the evoked response within the cardiac electrical signal.

22. The method of claim 14, further comprising, following delivery of the pacing pulse, using feedback to adjust a magnitude of the second voltage that is used to charge the pacing capacitor during the portion of the charge period, to thereby reduce, minimize or eliminate a polarization artifact superimposed on the evoked response within the cardiac electrical signal.

23. The method of claim 14, wherein the producing the plurality of different voltages comprises:

producing, using a first voltage generator, the first voltage;

producing, using a second voltage generator, a further voltage that is selectively added to the first voltage to produce the second voltage; and controlling when the further voltage is selectively added to the first voltage to produce the second voltage.

24. The method of claim 14, wherein the producing the plurality of different voltages comprises:

providing a first digital signal to a digital-to-analog converter (DAC) and amplifying a first analog signal that is output by the DAC to thereby produce the first voltage;

providing a second digital signal to the DAC and amplifying a second analog signal that is output by the DAC to thereby produce the second voltage; and controlling when the first and the second digital signals are provided to the DAC to thereby control when the first and the second voltages are produced.

25. The method of claim 14, wherein the producing the plurality of different voltages comprises:

producing the second voltage using a voltage generator;

providing the second voltage to an anode terminal of a diode;

producing the first voltage at a cathode terminal of the diode; and controlling when the second voltage that is provided to the anode terminal of the diode is used to charge the pacing capacitor, and when the first voltage that is produced at the cathode terminal of the diode is used to charge the pacing capacitor.

* * * * *